Figure 1:
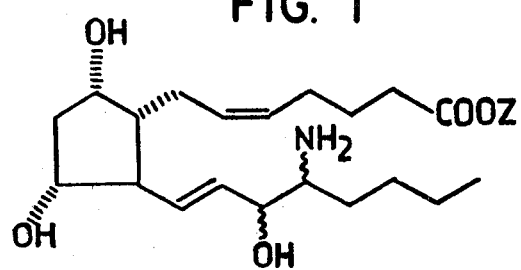
Figure 2:
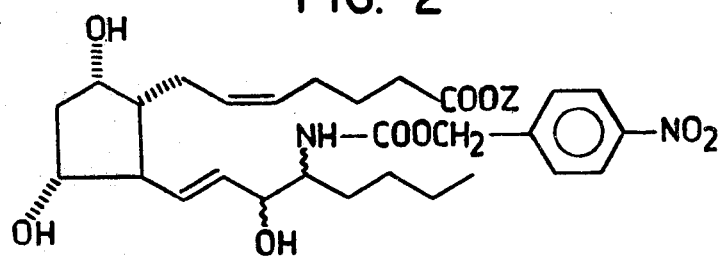

United States Patent [19]  [11]  4,372,973
Ambrus et al.  [45]  Feb. 8, 1983

[54] 16-AMINO-POSTAGLANDIN DERIVATIVES, THEIR ACID ADDITION SALTS, AND A PROCESS FOR THE PREPARATION THEREOF

[75] Inventors: Gabor Ambrus; Eva Toth-Sarudy; György Cseh; Istvan Barta; Gyula Horvath, all of Budapest, Hungary

[73] Assignee: Gyogyszerkutato Intezet, Budapest, Hungary

[21] Appl. No.: 332,840

[22] Filed: Dec. 21, 1981

Related U.S. Application Data

[63] Continuation-in-part of Ser. No. 265,433, May 20, 1981, abandoned.

[51] Int. Cl.$^3$ .................. A61K 31/557; C07C 177/00
[52] U.S. Cl. .................................. 424/305; 560/121; 562/503; 424/319
[58] Field of Search ................... 560/121; 562/503; 424/305, 319

[56] References Cited

U.S. PATENT DOCUMENTS 4,188,403 2/1980 Orth et al. ........................ 424/330

Primary Examiner—Robert Gerstl
Attorney, Agent, or Firm—Keil & Witherspoon

[57] ABSTRACT

The invention relates to new 16-amino-prostaglandin derivatives of general formula I,

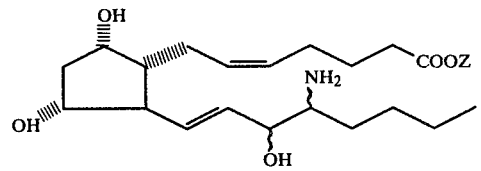

wherein C-15 and C-16 may have either S or R configuration, Z stands for a hydrogen atom or a lower alkyl group, and their acid addition salts. These compounds can be prepared by removing the ester group and the p-nitrocarbobenzyloxy protective group of a 9α, 11α, 15-trihydroxy-16-p-nitrobenzyloxycarbonylamido-5-cis,13-trans-prostadienoic acid derivative of general formula XII—wherein C-15 and C-16 may have either S or R configuration and Z stands for a lower alkyl group—in an optional sequence with the limitation that in those compounds of general formula I where Z stands for a lower alkyl group solely the p-nitrocarbobenzyloxy group is removed, and the resulting product of general formula I is optionally converted with an organic or inorganic acid into a salt.

The new prostaglandin derivatives of the invention have valuable therapeutical properties, and can be applied as abortive or oxytocic agents.

7 Claims, 13 Drawing Figures

FIG. 3
FIG. 4
FIG. 5
FIG. 6
FIG. 7
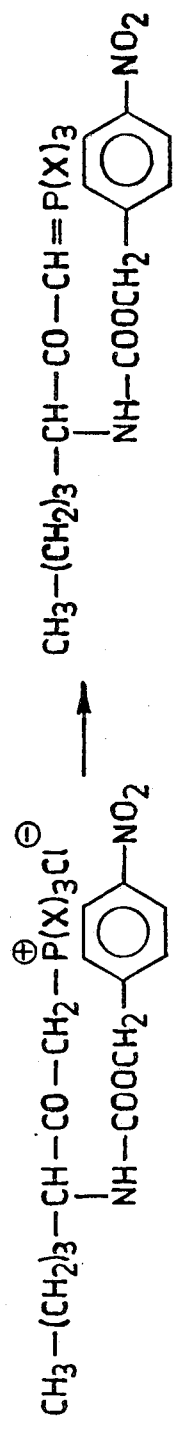
FIG. 8
FIG. 9

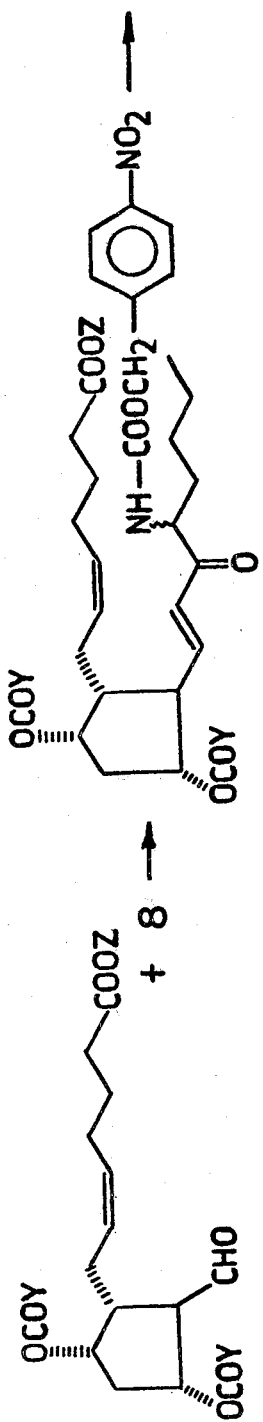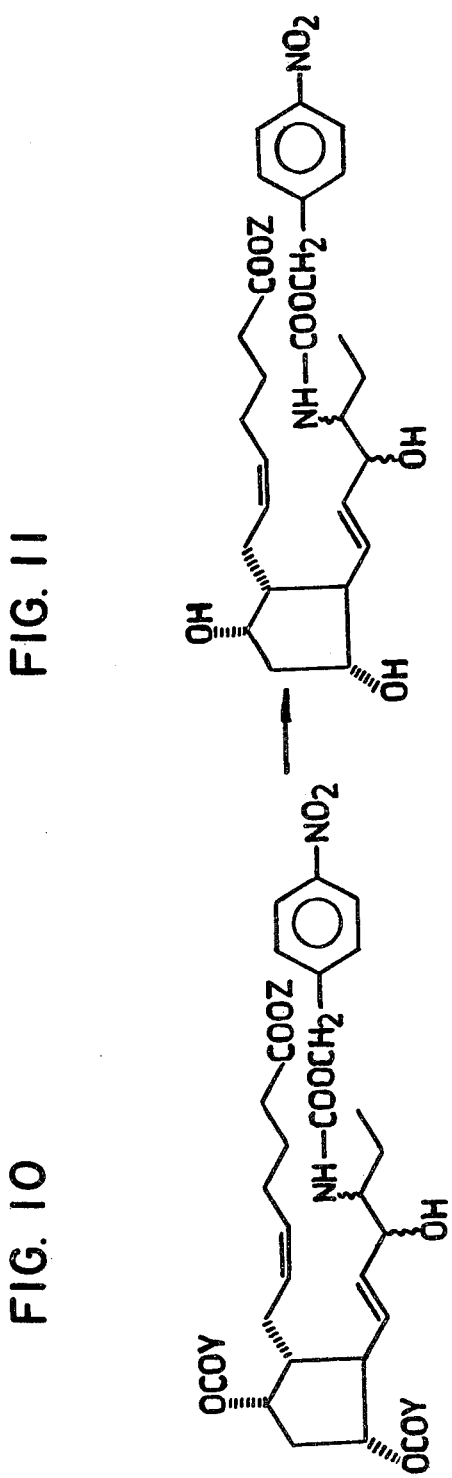
FIG. 10
FIG. 11
FIG. 12
FIG. 13

16-AMINO-POSTAGLANDIN DERIVATIVES, THEIR ACID ADDITION SALTS, AND A PROCESS FOR THE PREPARATION THEREOF

RELATED APPLICATION

This application is a continuation-in-part of our copending application Ser. No. 265,433, filed May 20, 1981, now abandoned.

INTRODUCTION

The invention relates to new 16-amino-prostaglandin derivatives of general formula I

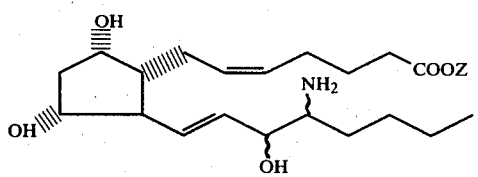

wherein:
C-15 and C-16 may have either S or R configuration, Z stands for a hydrogen atom or a lower alkyl group, and their acid addition salts. Furthermore, the invention relates to a process for the preparation of these compounds.

It is known that natural prostaglandins are rapidly metabolized in the organism with the simultaneous loss of their biological activity. The first step of the metabolic pathway is usually the enzymatic dehydrogenation of the 15-hydroxyl group of prostaglandin to a 15-oxo group. It is also known that chemical modifications performed on the C-15 group or in its vicinity have led to derivatives of natural prostaglandins which are resistant to any transformation induced by the enzyme 15-hydroxy-prostaglandin-dehydrogenase. Among these, derivatives having a methyl group either on C-15 or C-16 proved to be pharmaceutically valuable agents exhibiting a more prolonged and selective activity than natural prostaglandins themselves (G. L. Bundy et al.: Ann. N.Y. Acad. Sci. 180, 76, 1971; M. Hayashi et al.: J. Org. Chem. 38, 1250, 1973, B. J. Magerlein et al.: Prostaglandins 4, 1973.

THE INVENTION

In compliance with the invention the new 16-amino-prostaglandin derivatives of general formula I, wherein C-15 and C-16 may have either S or R configuration, Z stands for a hydrogen atom or a lower alkyl group, can be prepared by removing the ester group and the p-nitrobenzyloxycarbonyl protective group of a 9α, 11α, 15-trihydroxy-16-p-nitrobenzyloxycarbonyl-amido-5-cis, 13-trans-prostadienoic acid derivative of the general formula XII

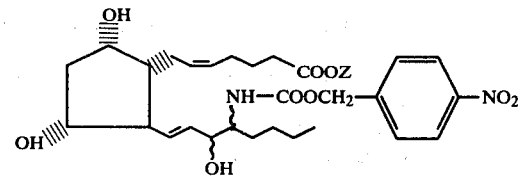

wherein:
C-15 and C-16 may have either S or R configuration and Z stands for a lower alkyl group—in an optional sequence with the limitation that in those compounds of general formula I where Z stands for a lower alkyl group solely the p-nitro-benzyloxycarbonyl group is removed, and the resulting product of general formula I is optionally converted with an organic or inorganic acid into a salt.

According to a preferred method the p-nitrobenzyloxycarbonyl group of a 9α, 11α, 15-trihydroxy-16-p-nitrobenzyloxycarbonyl-amido-5-cis-13-trans-prostadienoic acid derivative of general formula XII—wherein C-15 and C-16 may have either S or R configuration and Z has the same meaning as above—is removed in acetic acid with Zn dust and the ester group of the resulting 9α, 11α,15-trihydroxy-16-amino-5-cis-13-trans-prostadienoic acid ester is optionally hydrolyzed in a mixture of a lower alkanol, preferably methanol, and water with an alkali metal hydroxide, preferably lithium hydroxide, and treated with an acid until reaching the isoelectric point of the product. The isolated product can be converted into an acid addition salt by methods known per se. The Zn dust reduction in acetic acid is carried out within a temperature range of −5° C. to +10° C., preferably at 0° C., the ester hydrolysis between 0° C. to +10° C., preferably at +5° C.

The ester hydrolysis can advantageously be carried out by means of esterase enzymes such as Rhizopus oryzae lipase (Hungarian Pat. No. 160,109). In the course of the process of the invention the sequence of the removal of the p-nitrobenzyloxycarbonyl group and the ester group may be interchanged.

For preparing the acid addition salts of the compounds of general formula I a compound of general formula I possessing a free amino group, and obtained by the removal of the p-nitrobenzyloxycarbonyl protecting group, and optionally by the cleavage of the ester group, is preferably reacted in solution with an inorganic or organic acid or eventually with the solution thereof in a suitable solvent, and the acid addition salt formed is separated by methods known per se.

Compounds of general formula XII serving as starting materials of the process of the invention are also new. They can be synthesized in the following preferred way illustrated in the enclosed reaction scheme:

A p-nitrobenzyloxycarbonylnorleucine of general formula II—wherein the asymmetric carbon may be of either S or R configuration—is reacted with a chloroformic acid alkyl ester, the resulting mixed anhydride of formula III is converted with diazomethane to the 1-diazo-2-oxo-3-p-nitrobenzyloxycarbonylamidoheptane derivative of general formula IV. This is treated with hydrochloric acid, the resulting 1-chloro-2-oxo-3-p-nitrobenzyloxycarbonylamido-heptane of general formula V is reacted with a trisubstituted phosphine of general formula VI—wherein X stands for an alkyl or aryl group—and the resulting phosphonium chloride derivative of general formula VII—wherein X has the same meaning as above—is treated with an alkali metal hydroxide. The obtained phosphorane derivative of general formula VIII—wherein X has the same meaning as above—is reacted with 1α-(6-carbalkoxy-2-hexenyl)-2β-formyl-cyclopentane-3α, 5α-dioldiacylate of general formula IX, wherein Y stands for a lower alkyl or an aryl group and Z is a lower alkyl group. The resulting 9α,11α-diacyl-oxy-15-oxo-16-p-nitrobenzyloxycarbonylamido-5-cis, 13-trans-prostadienoic acid alkyl ester derivative of general formula X—wherein C-16 may have either S or R configuration, furthermore Y and Z have the same meaning as above—is reduced by an alkali metal borohydride. The reduction products of general formula XI, namely the 9α,11α-diacyloxy-15(S)-hydroxy-16-p-nitrobenzyloxycarbonylamido-5-cis, 13-trans-prostadienoic acid alkyl ester and the 9α,11α-diacyloxy-15(R)-hydroxy-16-p-nitrobenzyloxycarbonylamido-5-cis,1-trans-prostadienoic acid alkyl ester, wherein Z and Y have the same meaning as above, are separated and subsequently hydrolyzed in methanolic solution with p-toluenesulfonic acid.

In the synthesis of compounds having the general formula XII, which are starting materials in the process of the invention, it is preferred to use optically active 1α-(6-carbalkoxy-2-hexenyl)-2β-formyl-cyclopentane-3α,5α-diol-diacylate derivatives as key compounds. Starting from the known (-) 3α, 5α-dihydroxy-2β-(trityloxymethyl)-cyclopentane-1α-acetic acid γ-lactone (Tetrahedron Letters, 4639 (1976)), these compounds can advantageously be prepared in the following way:

The 3α,5α-dihydroxy-2β-(trityloxymethyl)-cyclopentane-1α-acetic acid-γ lactone is reduced by diizobutyl-aluminium-hydride, the obtained 3α, 5α-dihydroxy-2β-(trityloxymethyl)-cyclopentane-1α-acetaldehyde-γ lactol is reacted with 4-carboxy-butylidene-triphenyl-phosphorane, the obtained 1α-(6-carboxy-2-hexenyl)-2β-(trityloxymethyl)-cyclopentane-3α,5α-diol is esterified, the obtained 1α-(6-carbalkoxy-2-hexenyl)-2β-(trityloxymethyl)-cyclopentane-3α, 5α-diol is acylated with an acid chloride or acid anhydride obtained from an aliphatic or aromatic carboxylic acid, the resulting 1α-(6-carbalkoxy-2-hexenyl)-2β-(trityloxymethyl)-cyclopentane-3α, 5α-diol-diacylate is reacted with an organic or inorganic acid, and finally the obtained 1α-(6-carbalkoxy-2-hexenyl)-2β-hydroxymethyl-cyclopentane-3α,5α-diol-diacylate is submitted to oxidation (Hungarian Pat. No. 177,834.

The 1α-(6-carbalkoxy-2-hexenyl)-2β-formylcyclopentane-3α, 5α-diol-diacylates are preferred starting materials for preparing prostaglandin derivatives modified in their 3-hydroxy-1-trans-octenyl side chain, as these intermediary substances, being in the finishing stage of prostaglandin synthesis, can be easily converted into various prostaglandin analogues by suitably varying the Wittig-reagent utilized for sidechain formation.

The designations isomer A and isomer B are used for compounds having a different C-15 configuration appear at first with the hydroxyl derivatives of the general formula XI formed via the reduction of keto compounds of the general formula X. From among these compounds the one which in the course of layer chromatographic examinations proved to be more polar and which formerly was marked by 15(S) is isomer A and the less polar (nonpolar) compound is isomer B. Further on those compounds of the general formulas XII and I were named isomer A, too, which can be derived from the compounds of the general formula XI indicated as isomer A. (In case of the isomers B a similar procedure was followed.)

The Wittig-reagents required for preparing the prostaglandin derivatives of the present invention can be prepared from either S- or R-norleucine by the following reaction scheme:

In the course of the synthesis of 9α, 11α, 15(ksi)-trihydroxy-16(S)-amino-5-cis, 13-trans-prostadienoic acid (I, Z=H) the first step is the conversion of norleucine into its p-nitrobenzyloxycarbonyl derivative by a known method (D. T. Gish and F. H. Carpenter: J. Am. Chem. Soc. 75, 950 (1953)).

The p-nitrobenzyloxycarbonyl-S-norleucine is transformed in tetrahydrofuran in the presence of N-methyl-morpholine by the addition of a molar amount of isobutyl chloroformate at −15° C. into a mixed anhydride derivative. In the course of the reaction the N-methylmorpholine hydrochloride is precipitated. An excess of a solution of diazomethane in ether is added dropwise to this precipitated mixture and stirred for 3 hours at −15° C. Dry hydrogen chloride is led into the mixture containing the diazoketone derivative formed upon the reaction with diazomethane at −15° C. to obtain 1-chloro-2-oxo-3(S)-p-nitrobenzyloxycarbonylamidoheptane.

The 1-chloro-2-oxo-3(S)-p-nitrobenzyloxycarbonylamido-heptane is reacted in dichloromethane at boiling temperature with tri-n-butylphospine or trihenylphosphine, respectively. The phosphorane derivatives, utilized as Wittig-reagents, are set free from the resulting phosphonium salts by the addition of a solution of alkali metal hydroxide.

The 1α-(6-carbalkoxy-2-hexenyl)-2β-formylcyclopentane-3α, 5α-diol-diacylates are reacted in tetrahydrofuran for 3 hours with 2 moles of 3(S)-p-nitrobenzyloxycarbonylamido-2-oxo-heptylidene-tri-n-butyl-phosphorane. The 9α,11α-diacyloxy-15-oxo-16(S)-p-nitrobenzyloxycarbonylamido-5-cis, 13-trans-prostadienoic acid alkyl ester derivative, formed in the course of the reaction, is separated from the tri-n-butyl-phosphine oxide also formed in the reaction and from the remaining excess of 3(S)-p-nitrobenzyloxycarbonylamido-2-oxo-heptylidene-tri-n-butyl-phosphorane preferably by chromatography carried out on a silica gel column.

Reducing the 9α, 11α-diacyloxy-15-oxo-16(S)-p-nitrobenzyloxycarbonylamido-5-cis, 13-trans-prostadienoic acid alkyl ester derivative with an alkali metal borohydride, i.e., sodium borohydride, a mixture of 9α, 11α-diacyloxy-15(S)-hydroxy-16(S)-p-nitrobenzyloxycarbonylamido-5-cis, 13-trans-prostadienoic acid alkyl ester and 9α, 11α-diacyloxy-15(R)-hydroxy-16(S)-p-nitrobenzyloxycarbonylamido-5-cis, 13-trans-prostadienoic acid alkyl ester derivatives is formed. The two diastereomers, which differ from each other in the configuration of the C-15, can preferably be separated by thin-layer chromatography or column chromatography.

The 9α, 11α-diacyloxy-15(ksi)-hydroxy-16(S)-p-nitrobenzyloxycarbonylamido-5-cis, 13-trans-prostadienoic acid alkyl ester (isomer A) and the 9α, 11α-diacyloxy-15(ksi)-hydroxy-16(S)-p-nitrobenzyloxycarbonylamido-5-cis, 13-trans-prostadienoic acid alkyl ester (isomer B) derivatives are hydrolyzed in methanolic solution with p-toluenesulfonic acid at room temperature to 9α, 11α, 15(ksi)-trihydroxy-16(S)-p-nitrobenzyloxycarbonylamido-5-cis, 13-trans-prostadienoic acid alkyl ester and 9α, 11α, 15(ksi)-trihydroxy-16(S)-p-nitrobenzyloxycarbonylamido-5-cis, 13-trans-prostadienoic acid alkyl ester derivatives.

Following the above reaction scheme, then applying the process of the invention and starting from R-norleucine, 9α,11α, 15(ksi)-tri-hydroxy-16(R)-amino-5-cis, 13-trans-prostadienoic acid (isomer A) and 9α, 11α, 15(ksi)-trihydroxy-16(R)-amino-5-cis, 13-trans-prostadienoic acid (isomer B) as well as the respective lower alkyl esters of the above compounds were prepared.

The compounds prepared according to the process of the invention were submitted to several tests developed for detecting the effects of 9α, 11α, 15(S)-trihydroxy-5-cis, 13-trans-prostadienoic acid ($PGF_{2\alpha}$). From the organs containing smooth muscle guinea pig trachea, ileum and rat uterine horn were used in the trials. The organs were suspended in isotonic salt medium and the potency was registered on the basis of isotonic contractions (Pharmacological Experiments on Isolated Preparations, Ed. W. L. M. Perry and E. S. Livingstone, Edinburgh and London (1970)). The effect exerted on the aggregation of human blood platelets, induced by $5.10^{-5}$ mole/lit. of adenosine-5'-phosphate, was measured in a CHRONO LOG Aggregometer according to A. V. R. Born (J. Physiol. 162, 67 (1962)).

Beyond these tests it was determined according to P. Tolnay et al. (Acta Biochim. Biophys. Acad. Sci. Hung. 14, 67 (1979)) whether the compounds of the invention are substrates of the 15-hydroxy-prostaglandin-dehydrogenase enzyme.

The biological properties of the 16-amino-prostaglandin derivatives prepared according to the invention are substantially different from those of $PGF_{2\alpha}$ or its methyl ester used as controls, as is apparent from Table 1. It was established that the 16-amino-derivatives are no substrates of the 15-hydroxy-prostaglandin-dehydrogenase enzyme, consequently the enzyme does not inactivate them. The introduction of the amino group to C-16 failed to induce significant changes in the blood platelet inhibitory property, while the smooth muscle contraction triggering effect was reduced compared to $PGF_{2\alpha}$, although unexpectedly not at an identical rate, in the diverse organs. The 16(S)-amino-prostaglandin derivatives exhibit a more selective effect on the uterine muscle than $PFG_{2\alpha}$.

789 (1973)). In groups containing 5 animals the dose effect relationships of $PGF_{2\alpha}$, its methyl ester, as well as of the new 16-amino-prostaglandin derivatives were determined.

The potency of the new compounds prepared according to the invention proved to be significantly superior to that of $PGF_{2\alpha}$, the most active agent being 9 α, 11 α, 15(ksi)-trihydroxy-16(S)-amino-5-cis, 13-trans-prostadienoic acid methyl ester (isomer A). Its potency compared to the controls is summarized in Table 2, showing the 50% effective dose of the substances used for comparison.

TABLE 2

| Compound | $ED_{50}$/mg/kg body weight, s.c./ |
|---|---|
| $PGF_{2\alpha}$ | 20 |
| $PGF_{2\alpha}$ methyl ester | 6 |
| 9α,11α, 15 (ksi)-trihydroxy-16(S)-amino-5-cis,13-trans-prostadienoic acid methyl ester (isomer A) | 0.1. |

In addition to its exceedingly high abortive effect, 9 α, 11 α, 15(ksi)-trihydroxy-16(S)-amino-5-cis, 13-trans-prostadienoic acid methyl ester (isomer A) has a further favorable property. While abortive doses of both $PGF_{2\alpha}$ and its methyl ester exhibit also a laxative effect, no diarrhea is observed even at the tenfold of the abortive dose of the new 16(S)-amino-prostaglandin derivative.

Compounds prepared according to the process of the invention can be used to produce pharmaceutical formulations, by combining a 16-amino-prostaglandin de-

TABLE 1

| COMPOUND | 15-Hydroxy-prostaglandin-dehydrogenase In this test the concentration of the compounds $1.10^{-4}$ mole/lit. | Smooth muscle contraction | | | Inhibition of aggregation 100 μg/ml |
|---|---|---|---|---|---|
| | | Trachea[g] 1 μg/ml | relative efficiency Ileum[g] | Uterus[r] | % |
| $PGF_{2\alpha}$ | s | + | 1.00 | 1.00 | 82 |
| $PGF_{2\alpha}$ methyl ester | s | + | 0.78 | 1.25 | 56 |
| 9α,11α,15 (ksi)-trihydroxy-16(S)-amino-5-cis,13-trans-prostadienoic acid (isomer A) | O | ± | 0.11 | 0.83 | 75 |
| 9α,11α,15 (ksi)-trihydroxy-16(R)-amino-5-cis,13-trans-prostadienoic acid (isomer A) | O | O | 0.02 | 0.13 | |
| 9α,11α,15 (ksi)-trihydroxy-16(S)-amino-5-cis,13-trans-prostadienoic acid methyl ester (isomer A) | O | O | 0.17 | 0.99 | 52 |
| 9α,11α,15 (ksi)-trihydroxy-16(R)-amino-5-cis,15-trans-prostadienoic acid methyl ester (isomer A) | O | O | 0.02 | 0.05 | | s: substrate
O: inactive on trachea or no substrate of the enzyme
[g]guinea pig
[r]rat
+: contraction on trachea The favorable biological properties of the new compounds of the invention are clearly manifested in their abortive effect. The test materials were administered subcutaneously to white mice on the 17th or 18th day of pregnancy, then the deliveries were followed up in the subsequent 48 hours, and the overall status of the excised uterus (scars, embrional residual debris) was evaluated (M. J. R. Harper et al.: Advances in Biosciences 9, rivative of general formula I with a non-toxic, pharmaceutically acceptable, inert diluting agent and/or vehicle by usual methods applied in drug processing, thereby converting it into a pharmaceutical preparation.

A single dose of the compounds of the invention amounts to 0.2 to 1 mg s. c. or i. m., and 0.2 to 0.5 mg through an extraamnial catheter.

The invention is further illustrated by, but not limited to, the following Examples.

EXAMPLE 1

9α,11α,15(ksi)-Trihydroxy-16(S)-amino-5-cis, 13-trans-prostadienoic acid methyl ester (I, Z=CH₃, isomer A)

9α,11α,15(ksi)-Trihydroxy-16(S)-p-nitrobenzyloxycarbonylamido-5-cis, 13-trans-prostadienoic acid methyl ester, isomer A (1.7 g), is dissolved in acetic acid (27 ml), and water (9 ml) and Zn dust (980 mg) are added to the solution cooled to 0° C. at constant stirring. The reaction mixture is stirred for 1 hour at 0° C. under nitrogen, then its pH is adjusted with a 2 N sodium hydroxide solution to 6-7 at cooling and is freeze-dried. The solid residue is submitted to chromatography on a column prepared from silica-gel (60 g) (Kieselgel-40, Reanal, Budapest) in chloroform-methanol mixtures containing gradually increasing amounts of methanol. The product itself is eluted from the column with a mixture containing 12% of methanol. Yield: 930 mg of 9α,11α,15(ksi)-trihydroxy-16(S)-amino-5-cis, 13-trans-prostadienoic acid methyl ester (isomer A, 80%). IR spectrum (KBr): NH+OH 3600-3300, $\nu$ C=O 1730 cm⁻¹. NMR spectrum (DMSO-d₆): δ 0.88 (H-20, t, 3H), 2.70 (H-16, m, 1H), 3.62 (OCH₃, s, 3H), 3.70 (H-15, m, 1H), 3.94, 4.28 (H-9, 11, 2m, 2H), 5.30-5.60 (H-5,6,13,14, m, 4H) ppm.

Mass spectrum: MW (m/z): 383.

Mass number of characteristic ions (m/z): 383, 352, 334, 86. The hydrochloride of the aimed product melts at 153°-157° C., Cl-content: 8.36% (measured).

EXAMPLE 2

9α,1α,15(ksi)-Trihydroxy-16(S)-amino-5-cis, 13-trans-prostadienoic acid methyl ester (I, Z=CH₃, isomer B)

9α,11α,15(ksi)-Trihydroxy-16-(S)-p-nitrobenzyloxycarbonylamido-5-cis, 13-trans-prostadienoic acid methyl ester (isomer B, 840 mg) is dissolved in acetic acid (12 ml), and water (4 ml) and Zn dust (980 mg) are added to the solution cooled to 0° C. at constant stirring. The reaction mixture is stirred for 1 hour at 0° C. under nitrogen, then dichloromethane (10 ml) is added. The Zn dust is subsequently filtered off, and the filtrate concentrated to dryness at reduced pressure. The evaporation residue is submitted to chromatography on a column prepared from silicic acid (80 g) with dichloromethane-methanol mixtures containing gradually increasing amounts of methanol. The product is eluted from the column with a mixture containing 30% of methanol. Yield: 390 mg (68%) of 9α, 11α,15(ksi)-trihydroxy-16(S)-amino-5-cis,13-trans-prostadienoic acid methyl ester (isomer B). IR spectrum (KBr): $\nu$ NH+OH 3600-3100, $\nu$ C=O 1735 cm⁻¹. NMR spectrum (CDCl₃): δ 0.92 (H-20, t, 3H), 2.90 (H-16, m, 1H), 3.67 (OCH₃, s, 3H), 3.80-4.20 (H-9, 11,15, overlapping m, 3H), 5.42 (H-5.6, m, 2H), 5.64 (H-13,14, m, 2H) ppm.

Mass spectrum: MW (m/z): 383.

Mass number of characteristic ions (m/z): 383, 352, 334, 86.

The starting materials of Examples 1 and 2 can be prepared according to the following process:

(a)
1-chloro-2-oxo-3(S)-p-nitrobenzyloxycarbonylamido-heptane (V)

p-nitrobenzyloxycarbonyl-S-norleucine (1.5 g) is dissolved in tetrahydrofuran (24 ml) and at −15° C. N-methylmorpholine (0.54 ml) and isobutyl chloroformate (0.64 ml) are added to the solution. The reaction mixture is stirred at −15° C. for 30 minutes, then a 2% etheral solution of diazomethane (25 ml) is added dropwise to the mixed anhydride obtained. The reaction mixture is stirred for 3 more hours at −15° C., then dry hydrogen chloride is led into the solution of the diazoketone derivative, which is finally evaporated to dryness under reduced pressure. The residual oil is mixed with n pentane (20 ml) and the white crystals formed are filtered and dried at reduced pressure. The product obtained is homogeneous in thin-layer chromatography (adsorbent: Kieselgel G and Kieselgel 60 HF 254+366 according to Stahl, Reanal, Budapest, developing system: ethyl-acetate-n-heptane 30:70, $R_F$=0.41). Yield: 1.57 g (95%) of 1-chloro-2-oxo-3(S)-p-nitrobenzyloxycarbonylamido-heptane.

M.p.: 72°-75° C.

IR spectrum (KBr): $\nu$ NH 3300, $\nu$ C=O (ketone) 1730, $\nu$ C=O (amide) 1685 cm⁻¹.

NMR spectrum (CDCl₃): δ 0.92 (CH₃, t, 3H), 4.18 (CH₂Cl, s, 2H), 4.60 (CH-NH, m, 1H), 5.20 (CH₂-Ar-NO₂, s, 2H), 5.5 (NH, d, 1H), 7.46, 8.13 (Ar-H, AA'XX' m, J=9 Hz, 4H) ppm.

(b)
9α,11α-Diacetoxy-15-oxo-16(S)-p-nitrobenzyloxycarbonylamido-5-cis,13-trans-prostadienoic acid methyl ester (X,Y=Z=CH₃)

Tri-n-butylphosphine (5.4 ml) is added under stirring to a solution of 1-chloro-2-oxo-3(S)-p-nitrobenzyloxycarbonylamido-heptane (6.8 g) in dichloromethane (70 ml) and the reaction mixture is heated to 60° C. for 2 hours, then evaporated to dryness at reduced pressure. Water is poured over the residue (50 ml), and the unreacted tri-n-butyl-phosphine is extracted twice with n-heptane (30 ml). Diethylether (20 ml) is added to the aqueous layer containing the 2-oxo-3(S)-p-nitrobenzyloxycarbonylamido-heptyl-tri-n-butyl-phosphonium chloride and 2 N sodium hydroxide is added dropwise (10 ml) under cooling (5° C.) and the reaction mixture obtained is stirred for 6 minutes. Then the aqueous layer is separated and extracted twice with ether (10 ml). The combined ethereous extracts are dried over anhydrous sodium sulfate and evaporated to 10 ml at reduced pressure. This solution of 2-oxo-3(S)-p-nitrobenzyloxycarbonylamido-heptylidene-tri-n-butyl-phosphorane in ether is added at 5° C., under stirring and under nitrogen to a solution of 1α-(6-carbomethoxy-2-hexenyl)-2β-formyl-cyclopentane-3α, 5α-diol-diacetate (3.55 g) in tetrahydrofuran (25 ml). After evaporation of the ether the reaction mixture is stirred at 20° C. for 3 hours, then the solvent is evaporated at reduced pressure. The residue is submitted to chromatography on a silicic acid column (200 g) with a solvent system of n-hexane-ethylacetate containing gradually increasing amounts of ethylacetate. The product is eluted from the column with a mixture containing 12% of ethyl-acetate. Yield: 5.8 g (90%) of 9α,11α-diacetoxy-15-oxo-16(S)-p-nitrobenzyloxycarbonylamido-5-cis, 13-trans-prostadienoic acid methyl ester (oil). IR spectrum (film): $\nu$ NH 3410-3340, $\nu$ C=O 1730, $\nu$ C=C 1630 cm⁻¹.

NMR spectrum (CDCl$_3$): 0.89 (H-20, t, 3H), 2.00, 2.08 (CH$_3$CO, 2s, 2×3H), 3.65 (OCH$_3$, s, 3H), 4.65 (H-16, m, 1H), 5.22 (CH$_2$—Ar—NO$_2$, s, 2H), 4.80–5.5 (H-5,6,7,11, m, 4H), 6.27 (H-14, d, 1H), 6.88 (H-13, dd, 1H), 7.50, 8.20 (Ar-H, AA′XX′ m, J$_A$=9 Hz, 4H), ppm.

Mass spectrum: MW (m/z): 644.

Mass number of characteristic ions (m/z): 644, 584, 524, 337, 319, 265, 259, 221.

(c) 9α,11α-Diacetoxy-15(ksi)-hydroxy-16(S)-p-nitrobenzyloxycarbonylamido-5-cis,13-trans-prostadienoic acid methyl ester (isomer A) and 9α,11α-diacetoxy-15(ksi)-hydroxy-16(S)-p-nitrobenzyloxycarbonylamido-5-cis,13-trans-prostadienoic acid methyl ester (isomer B) (XI, Y=Z=CH$_3$)

Sodium borohydride (323 mg) is added at 5° C. and stirring to a solution of 9α,11α-diacetoxy-15-oxo-16(S)-p-nitrobenzyloxycarbonylamido-5-cis, 13-trans-prostadienoic acid methyl ester (5.5 g) in methanol (100 ml). The reaction mixture is stirred at 5° C. under nitrogen for 1 hour, then is poured into a 0.2 M sodium dihydrogen phosphate solution (500 ml) cooled to 5° C., and extracted three times with ethylacetate (150 ml). The combined ethylacetate extracts are dried over anhydrous sodium sulfate and evaporated at reduced pressure. The crude product obtained is purified by preparative thin-layer chromatography, applying silica gel is adsorbent (Kieselgel G and Kieselgel 60 HF 254+366, according to Stahl, Reanal, Budapest) and a mixture of n-hexane-ethylacetate 1:1 as developing solvent. Yield: 3.2 g of 9α,11α-diacetoxy-15(ksi)-hydroxy-16(S)-p-nitrobenzyloxycarbonylamido-5-cis,13-trans-prostadienoic acid methyl ester (polar product, isomer A) and 1.8 g of 9α,11α-diacetoxy-15(ksi)-hydroxy-16(S)-p-nitro-benzyloxycarbonylamido-5-cis,13-trans-prostadienoic acid methyl ester (apolar product, isomer B). 9α,11α-Diacetoxy-15(ksi)-hydroxy-16(S)-p-nitrobenzyl-oxycarbonylamido-5-cis,13-trans-prostadienoic acid methyl ester (oil, isomer A):

IR spectrum (film): ν HN 3440, 3360, ν C=O 1735 cm$^{-1}$. NMR spectrum (CDCl$_3$): δ 0.89 (H-20, t, 3H), 2.00 2.08 (CH$_3$CO, 2s, 2×3H), 3.65 (OCH$_3$, s, 3H), 3.75 (H-16, m,1H), 4.25 (H-15, m, 1H), 4.6–5.25 (H-9, 11, overlaping m, 2H), 5.20 (CH$_2$—Ar—NO$_2$, s 2H), 5.36 (H-5.6, m, 2H), 5.61 (H-13,14, m, 2H), 7.50, 8.20 (Ar-H, AA′XX′ m, J$_{AX}$=9 Hz, 4H) ppm.

Mass spectrum: mass number of characteristic ions (m/z): 628, 615, 381, 321, 265, 221. 9α,11α-Diacetoxy-15(ksi)-hydroxy-16(S)-p-nitrobenzyl-oxycarbonylamido-5-cis,13-trans-prostadienoic acid methyl ester (oil, isomer B):

IR spectrum (film): ν OH+NH 3500-3360, ν C=O 1740 cm$^{-1}$.

NMR spectrum (CDCl$_3$): δ 0.88 (H-20, t, 3H), 2.00, 2.07 (CH$_3$CO, 2s, 2×3H), 3.5–3.8 (H-16, overlapping m, 1H), 3.65 (OCH$_3$, s, 3H), 4.18 (H-15, m, 1H), 4.85–5.30 (H-9,11, overlapping m, 2H), 5.20 (CH$_2$Ar-NO$_2$, s, 2H), 5.35 (H-5,6,m, 2H), 5.6 (H-13,14, m, 2H), 7.48, 8.15 (Ar-H, AA′XX′ m, J$_{AX}$=9 Hz, 4H) ppm.

Mass spectrum: mass number of characteristic ions (m/z): 628, 615, 381, 321, 265, 221.

(d)$_1$

9α,11α,15(ksi)-Trihydroxy-16-(S)-p-nitrobenzyloxycarbonylamido-5-cis,13-trans-prostadienoic acid methyl ester (XII, Z=CH$_3$, isomer A)

9α,11α-Diacetoxy-15(ksi)-hydroxy-16(S)-p-nitrobenzyloxycarbonylamido-5-cis,13-trans-prostadienoic acid methyl ester (isomer A, 3 g) is dissolved in anhydrous methanol (200 ml) and p-toluenesulfonic acid monohydrate (7 g) is added to the solution. The reaction mixture is stirred under nitrogen, at room temperature, for 24 hours, then is poured into a 1 M solution of disodium hydrogen phosphate (350 ml) (pH=6), and extracted three times with ethylacetate (80 ml). The combined ethylacetate extracts are evaporated under reduced pressure. The residue is submitted to preparative thin-layer chromatography, applying silica gel as adsorbent (Kieselgel G and Kieselgel 60 HF 254+366 according to Stahl, Reanal, Budapest) and a mixture of chloroform-ethanol (95:5) as developing solvent. Yield: 2 g of chromatographically pure 9α,11α,15(ksi)-trihydroxy-16(S)-p-nitrobenzyloxycarbonylamido-5-cis,13-trans-prostadienoic acid methyl ester (isomer A, 76%):

M. p.: 55°–58° C.

IR spectrum (KBr): ν NH+OH 3420-3320, ν C=O 1715, 1690 cm$^{-1}$.

NMR spectrum (CDCl$_3$): δ 0.88 (H-20, t, 3H), 3.65 (OCH$_3$, s, 3H), 3.60–4.15 (H-9,11,15,16, overlapping m, 4H), 5.20 (CH$_2$—Ar—NO$_2$, s, 2H), 5.40 (H-5,6, m, 2H), 5.62 (H-13,14, m, 2H), 7.50, 8.18 (Ar-H, AA′XX′ m, J$_{AX}$=9 Hz, 4H) ppm.

Mass spectrum: mass number of characteristic ions (m/z): 544, 526, 513, 297, 265, 221.

(d)$_2$

9α,11α,15(ksi)-Trihydroxy-16(S)-p-nitrobenzyloxycarbonylamido-5-cis,13-trans-prostadienoic acid methyl ester (XII, Z=CH$_3$, isomer B)

9α,11α-Diacetoxy-15(ksi)-hydroxy-16(S)-p-nitrobenzyloxycarbonylamido-5-cis,13-trans-prostadienoic acid methyl ester (isomer B, 1.6 g) is dissolved in anhydrous methanol (90 ml) and mixed with p-toluenesulfonic acid monohydrate (3.7 g). The reaction mixture is stirred under nitrogen at room temperature for 24 hours, and the product formed is isolated according to the procedure described in step d$_1$. Yield: 1.1 g (78%) of 9α,11α,15(ksi)-trihydroxy-16(S)-p-nitrobenzyloxycarbonylamido-5-cis,13-trans-prostadienoic acid methyl ester (oil, isomer B).

IR spectrum (KBr): ν NH+OH 3400, ν C=O 1720 cm$^{-1}$.

NMR spectrum (CDCl$_3$): δ 0.90 (H-20, t, 3H), 3.65 (OCH$_3$, s, 3H), 3.6–4.3 (H-9,11,15,16, m, 4H), 5.20 (CH$_2$-Ar-NO$_2$, s, 2H), 5.40 (H-5,6, m, 2H), 5.63 (H-13,14, m, 2H), 7.52, 8.20 (Ar-H, AA′XX′ m, J$_{AX}$=9 Hz, 4H) ppm.

Mass spectrum: mass number of characteristic ions (m/z): 544, 526, 513, 297, 265, 221.

EXAMPLE 3

9α,11α,15(ksi)-Trihydroxy-16(S)-amino-5-cis, 13-trans-prostadienoic acid (I, Z=H, isomer A)

Lithium hydroxide (720 mg), dissolved in water (12 ml), is added at 0° C. to a solution of 9α, 11α,15(ksi)-trihydroxy-16(S)-amino-5-cis,13-trans-prostadienoic acid methyl ester (isomer A, 767 mg) in methanol (36 ml). The reaction mixture is stirred under nitrogen, at 0° C. for 8 hours, then the pH of the solution is adjusted with 8% aqueous oxalic acid to 6. The methanol is evaporated at 5° C. at reduced pressure, and the remaining aqueous solution is freeze-dried. The dry residue is submitted to chromatography on a silica-gel column (20 g) (Kieselgel 40, Reanal, Budapest) with a system of chloroform-methanol, containing gradually increasing amounts of methanol. The product is eluted from the column by a mixture containing 30% of methanol. Yield: 665 mg (90%) of pure 9α,11α, 15(ksi)-trihydroxy-16(S)-amino-5-cis, 13-trans-prostadienoic acid (isomer A).

IR Spectrum (KBr): ν NH+OH 3600-2500, ν C=O 1710 cm$^{-1}$.

NMR spectrum (DMSO-d$_6$): δ 0.88 (H-20,t,3H), 3.00 (H-16, m, 1H), 3.70 (H-15, m, 1H), 3.96, 4.26 (H-9,11, 2m, 2H), 5.38 (H-5,6, m, 2H), 5.56 (H-13,14, m, 2H) ppm.

Mass spectrum: MW (m/z): 369.

Mass number of characteristic ions (m/z): 369, 352, 334, 86.

EXAMPLE 4

9α,11α,15(ksi)-Trihydroxy-16(S)-amino-5-cis, 13-trans-prostadienoic acid (I, Z=H, isomer B)

Lithium hydroxide (250 mg), dissolved in water (4 ml), is added at 0° C. to a solution of 9α, 11α,15(ksi)-trihydroxy-16(S)-amino-5-cis, 13-trans-prostadienoic acid methyl ester (isomer B, 270 mg), in methanol (12 ml). The reaction mixture is stirred under nitrogen at 0° C. for 10 hours, then the product is isolated according to the procedure described in Example 3. Yield: 230 g (88%) of chromatographically pure 9α, 11α,15(ksi)-trihydroxy-16(S)-amino-5-cis, 13-trans-prostadienoic acid (isomer B).

IR spectrum (KBr): ν NH+OH 3600-2500, ν C=O 1710 cm$^{-1}$.

NMR spectrum (DMSO-d$_6$): δ 0.89 (H-20, t, 3H), 2.90 (H-16, m, 1H), 3.72 (H-15, m, 1H), 3.86-4.16 (H-9,11, m, 2H), 5.4 (H-5,6, m, 2H), 5.58 (H-13,14, m, 2H), ppm.

Mass spectrum: MW (m/z): 369.

Mass number of characteristic ions (m/z): 369, 352, 334, 86.

EXAMPLE 5

9α,11α,15(ksi)-Trihydroxy-16(S)-amino-5-cis, 13-trans-prostadienoic acid (I, Z=H, isomer A)

9α,11α,15(ksi)-Trihydroxy-16(S)-p-nitrobenzyloxycarbonylamido-5-cis,13-trans-prostadienoic acid methyl ester (isomer A, 350 mg), Rhizopus oryzae lipase enzyme (60 mg), acacia gum (350 mg), and sodium taurocholate (15 mg) are added to a 0.1 M phosphate buffer (20 ml, pH 8). The suspension is shaken on a rotary shaker at 28° C. for 2 days, then diluted with water (100 ml), acidified with citric acid to pH 3 and extracted 3 times with ethylacetate (20 ml). The combined ethylacetate extracts are evaporated at reduced pressure. The residue, containing the 9α,11α,15(ksi)-trihydroxy-16(S)-p-nitrobenzyloxycarbonylamido-5-cis,13-trans-prostadienoic acid (isomer A), is dissolved in 70% aqueous acetic acid (5 ml), cooled to 0° C., and stirred at this temperature under nitrogen for 1 hour with Zn dust (350 mg). Then the reaction mixture is diluted with dichloromethane (20 ml), the Zn dust filtered off, and the filtrate evaporated at reduced pressure. The residue is submitted to chromatography on a column prepared from silicic acid (5 g), in a system of chloroform-methanol containing gradually increasing amounts of methanol. The produce itself is eluted from the column with a mixture containing 70% of methanol. Yield: 105 mg (46%) of 9α,11α,15(ksi)-trihydroxy-16(S)-amino-5-cis,13-trans-prostadienoic acid.

EXAMPLE 6

9α,11α,15(ksi)-Trihydroxy-16(R)-amino-5-cis, 13-trans-prostadienoic acid methyl ester (I, Z=CH$_3$, isomer A)

Zn dust (330 mg) and water (3 ml) are added to a solution of 9α,11α,15(ksi)-trihydroxy-16(R)-p-nitrobenzyloxycarbonylamido-5-cis,13-trans-prostadienoic acid methyl ester (isomer A, 560 mg) in acetic acid (9 ml) cooled to 0° C. The reaction mixture is stirred under nitrogen at 0° C. for 1 hour, then the pH of the solution is adjusted under cooling with 2 N sodium hydroxide to 6-7, and freeze-dried. The solid residue is submitted to chromatography on a column prepared of silica gel (12 g, Kieselgel 40, Reanal, Budapest) with a system of chloroform-methanol containing gradually increasing amounts of methanol. The product is eluted from the column with a mixture containing 12% of methanol. Yield: 300 mg (79%) of 9α,11α,15(S)-trihydroxy-16(R)-amino-5-cis, 13-trans-prostadienoic acid methyl ester (isomer A).

M. p.: 63°-67° C.

IR spectrum (KBr): ν NH+OH 3350, ν C=O 1740 cm$^{-1}$.

NMR spectrum (DMSO-d$_6$+TFA): δ 0.9 (H-20, t, 3H), 3.15 (H-16, m, 1H), 3.6 (OCH$_3$, s, 3H), 3.6-4.0 (H-9,11,15, m, 3H), 5.2-5.6 (H-5,6,13,14, m, 4H) ppm.

Mass spectrum: MW (m/z): 383.

Mass number of characteristic ions (m/z): 383, 352, 334, 86.

EXAMPLE 7

9α,11α,15(ksi)-Trihydroxy-16(R)-amino-5-cis, 13-trans-prostadienoic acid methyl ester (I, Z=CH$_3$, isomer B)

Zn dust (820 mg) and water (7 ml) are added at constant stirring to a solution of 9α,11α,15(ksi)-trihydroxy-16(R)-p-nitrobenzyloxycarbonylamido-5-cis, 13-trans-prostadienoic acid methyl ester (1.4 g, isomer B) in acetic acid (21 ml) at 0° C. The reaction mixture is stirred under nitrogen at 0° C. for 1 hour and the product is subsequently isolated according to the procedure described in Example 6. Yield: 710 mg (74%) of 9α,1-1α,15(ksi)-trihydroxy-16(R)-amino-5-cis, 13-trans-prostadienoic acid methyl ester (isomer B).

IR spectrum (KBr): ν NH+OH 3560, 3350, ν C=O 1730 cm$^{-1}$.

NMR spectrum (DMSO-d$_6$): δ 0.9 (H-20, t, 3H), 3.1 (H-16, m, 1H), 3.6 (OCH$_3$, s, 3H), 3.9, 4.3 (H-9,11,15, m, 3H), 5.1-5.7 (H-5,6,13,14, m, 4H) ppm.

Mass spectrum: MW (m/z): 383.

Mass number of characteristic ions (m/z): 383, 352, 334, 86.

The preparation of the starting materials of Examples 6 and 7, namely of 9α,11α,15(ksi)-trihydroxy-16(R)-p-nitrobenzyloxycarbonylamido-5-cis, 13-trans-prostadienoic acid methyl ester and of 9α,11α,15(ξ)-trihydroxy-16(R)-p-nitrobenzyloxycarbonylamido-5-cis, 13-trans-prostadienoic acid methyl ester (isomer B), can be carried out according to the procedure described for the starting materials of Examples 1 and 2, except that p-nitrobenzyloxycarbonyl-R-norleucine is used as starting material.

The physical and spectroscopical data of the compounds prepared are summarized in the following:

(a)
1-Chloro-2-oxo-3(R)-p-nitro-benzyloxycarbonylamido-heptane (V)

M.p.: 72°–75° C.

IR spectrum (KBr): $\nu$ NH 3300, $\nu$ C=O (ketone) 1735, $\nu$ C=O (amide) 1690 cm$^{-1}$.

NMR spectrum (CDCl$_3$): $\delta$ 0.9 (CH$_3$, t, 3H), 4.25 (CH$_2$Cl, s, 2H), 4.6 (CH–NH, m, 1H), 5.25 (CH$_2$-Ar-NO$_2$, s, 2H), 5.55 (NH, d, 1H), 7.45, 8.2 (Ar-H, AA'XX' m, J=9 Hz, 4H) ppm.

(b)
9α,11α-Diacetoxy-15-oxo-16(R)-nitrobenzyloxycarbonylamido-5-cis,13-trans-prostadienoic acid methyl ester (oil) (X, Y=Z=CH$_3$)

IR spectrum (film): $\nu$ NH 3350, $\nu$ C=O 1730, $\nu$ C=C 1630 cm$^{-1}$.

NMR spectrum (CDCl$_3$): $\delta$ 0.88 (H-20, t, 3H), 2.00, 2.08 (CH$_3$CO, 2s, 2×3H), 3.67 (OCH$_3$, s, 3H), 4.65 (H-16, m, 1H), 5.20 (CH$_2$-Ar-NO$_2$), s, 2H), 4.85–5.5 (H-5,6,9,11, m, 4H), 6.28 (H-14, d, 1H), 6.90 (H-13, dd, 1H), 7.52, 8.22 (Ar-H, AA'XX' m, J$_{AX}$=9 Hz, 4H) ppm.

Mass spectrum: MW (m/z): 644.

Mass number of characteristic ions (m/z): 644, 584, 524, 337, 319, 265, 259, 221.

(c)
9α,11α-Diacetoxy-15(ksi)-hydroxy-16(R)-p-nitrobenzyloxycarbonylamido-5-cis,13-trans-prostadienoic acid methyl ester (oil) (XI, Y=Z=CH$_3$, isomer A)

IR spectrum (film): $\nu$ NH 3400, $\nu$ C=O 1730 cm$^{-1}$.

NMR spectrum (CDCl$_3$): $\delta$ 0.90 (H-20, t, 3H), 2.00, 2.07 (CH$_3$CO, 2s, 2×3H), 3.65 (OCH$_3$, s, 3H), 3.7 (H-16, m, 1H), 4.2 (H-15, m, 1H), 4.8–5.25 (H-9,11, overlapping m, 2H), 5.20 (CH$_2$-Ar-NO$_2$, s, 2H), 5.38 (H-5,6, m, 2H), 5.65 (H-13,14, m, 1H), 7.52, 8.23 (Ar-H, AA'XX' m, J$_{AX}$=9 Hz, 4H) ppm.

Mass spectrum: mass number of characteristic ions (m/z): 628, 615, 381, 321, 265, 221.

9α,11α-Diacetoxy-15(ksi)-hydroxy-16(R)-p-nitrobenzyloxycarbonylamido-5-cis, 13-trans-prostadienoic acid methyl ester (oil) (XI, Y=Z=CH$_3$, isomer B)

IR spectrum (film): $\nu$ NH+OH 3600–3200, $\nu$ C=O 1720 cm$^{-1}$.

NMR spectrum (CDCl$_3$): $\delta$ 0.89 (H-20, t, 3H), 1.98, 2.05 (CH$_3$CO- 2s, 2×3H), 3.76 (H-16, m, 1H), 3.65 (OCH$_3$, s, 3H), 4.23 (H-15, m, 1H), 4.8–5.2 (H-9,11, m, 2H), 5.20 (CH$_2$-Ar-NO$_2$, s, 2H), 5.38 (H-5,6, m, 2H), 5.63 (H-13,14, m, 2H), 7.53, 8.22 (Ar-H, AA'XX' m, J$_{AX}$=9 Hz, 4H) ppm.

Mass spectrum: mass number of characteristic ions (m/z): 628, 615, 381, 321, 265, 221.

(d$_1$)
9α,11α,15(ksi)-Trihydroxy-16(R)-p-nitrobenzyloxycarbonylamido-5-cis, 13-trans-prostadienoic acid methyl ester (XII, Z=CH$_3$, isomer A)

IR spectrum (film): $\nu$ NH+OH 3400, $\nu$ C=O 1720–1690 cm$^{-1}$.

NMR Spectrum (CDCl$_3$): $\delta$ 0.88 (H-20, t, 3H), 3.65 (OCH$_3$, s, 3H), 3.5–4.0, 4.16 (H-9,11,15,16, m, 4H), 5.18 (CH$_2$—Ar—NO$_2$, s, 2H), 5.40 (H-5,6, m, 2H), 5.60 (H-13,14, m, 2H), 7.50, 8.20 (Ar-H, AA'XX' m, J$_{AX}$=9 Hz, 4H) ppm.

Mass spectrum: mass number of characteristic ions (m/z): 544, 526, 513, 297, 265, 221.

(d$_2$)
9α,11α,15(ksi)-Trihydroxy-16(R)-p-nitrobenzyloxycarbonylamido-5-cis,13-trans-prostadienoic acid methyl ester (XII, Z=CH$_3$, isomer B)

M. p.: 68°–72° C.

IR spectrum (KBr): $\nu$ NH+OH 3380, $\nu$ C=O 1720 cm$^{-1}$.

NMR spectrum (CDCl$_3$): $\delta$ 0.88 (H-20, t, 3H), 3.65 (OCH$_3$, s, 3H), 3.6–4.0, 4.18 (H-9,11,15,16, m, 4H), 5.20 (CH$_2$—Ar—NO$_2$, s, 2H), 5.40 (H-5,6, m, 2H), 5.62 (H-13,14, m, 2H), 7.50, 8.20 (Ar-H, AA'XX' m, J$_{AX}$=9 Hz, 4H) ppm.

Mass spectrum: mass number of characteristic ions (m/z): 544, 526, 513, 297, 265, 221.

EXAMPLE 8

9α,11α,15(ksi)-Trihydroxy-16(R)-amino-5-cis, 13-trans-prostadienoic acid (I, Z=H, isomer A)

Lithium hydroxide (235 mg), dissolved in water (4 ml), is added at 0° C. to a solution of 9α,11α,15(ksi)-trihydroxy-16(R)-amino-5-cis, 13-trans-prostadienoic acid methyl ester (isomer A, 250 mg) in methanol (12 ml). The reaction mixture is stirred under nitrogen at 0° C. for 10 hours, then the pH of the solution is adjusted with 8% aqueous oxalic acid to 6. The methanol is evaporated at 5° C. at reduced pressure and the residual aqueous solution is freeze-dried. The dry residue is submitted to chromatography on a column prepared of silica gel (10 g) with a system of chloroform-methanol, containing gradually increasing amounts of methanol. The product is eluted from the column with a mixture containing 30% of methanol. Yield: 210 mg (87%) of chromatographically pure 9α,11α, 15(ksi)-trihydroxy-16(R)-amino-5-cis,13-trans-prostadienoic acid (isomer A).

IR spectrum (film): $\nu$ NH+OH 3300, $\nu$ C=O 1720, $\nu$ COO$^-$ 1570 (b) cm$^{-1}$.

NMR spectrum (DMSO-d$_6$): $\delta$ 0.9 (H-20, t, 3H), 2.9 (H-16, m, 1H), 3.9–4.3 (H-9,11,15, m, 3H), 5.2–5.6 (H-5,6,13,14, m, 4H) ppm.

Mass spectrum: MW (m/z): 369.

Mass number of characteristic ions (m/z): 369, 352, 334, 86.

EXAMPLE 9

9α,11α,15(ksi)-Trihydroxy-16(R)-amino-5-cis, 13-trans-prostadienoic acid (I, Z=H, isomer B)

Lithium hydroxide (540 mg), dissolved in water (8 ml), is added at 0° C. to a solution of 9α,11α,15(ksi)-trihydroxy-16(R)-amino-5-cis, 13-trans-prostadienoic acid methyl ester (isomer B) in methanol (24 ml). The reaction mixture is stirred at 0° C. under nitrogen for 10 hours, then the product is isolated according to the procedure described in Example 8. Yield: 500 mg (90%) of chromatographically pure 9α,11α,15(ksi)-trihydroxy-16(R)-amino-5-cis-13,trans-prostadienoic acid (isomer B).

M. p.: 88° C.

IR spectrum (KBr): $\nu$ NH+OH 3300, $\nu$ C=O 1720, $\nu$ COO$^-$ 1570 (b) cm$^{-1}$.

NMR spectrum (DMSO-d$_6$): $\delta$ 0.9 (H-20, t, 3H), 2.9 (H-16, m, 1H), 3.7–4.2 (H-9,11,15, m, 3H), 5.4–5.8 (H-5,6,13,14, m, 4H) ppm.

Mass spectrum: MW (m/z): 369.

Mass number of characteristic ions (m/z): 369, 352, 334, 86.

EXAMPLE 10

Preparation of a pharmaceutical composition

Freeze-dried ampoules are prepared for injections as follows: 9α,11α,15(ksi)-Trihydroxy-16(S)-amino-5-cis, 13-trans-prostadienoic acid methyl ester (isomer A, 0.2 mg) is freeze-dried together with mannitol (2 mg). The contents of these freeze-dried ampoules are dissolved in 1 ml of a sterile, isotonic sodium chloride solution prior to application.

FORMULAE (I) to (XII)

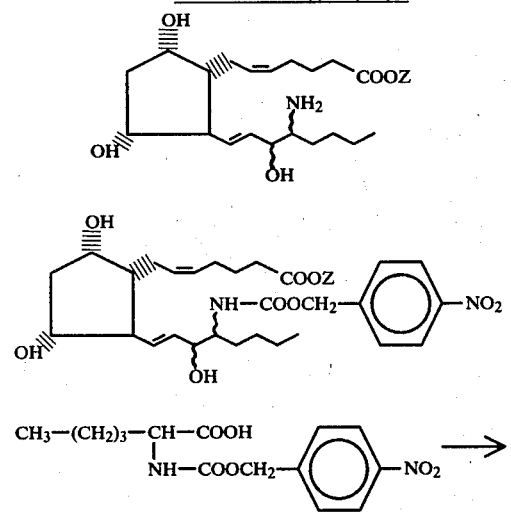

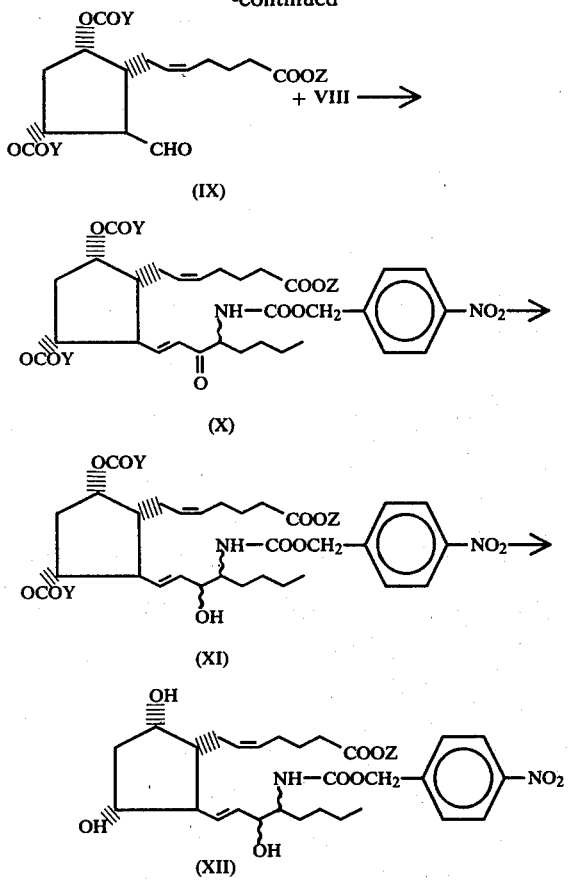

What we claim is:

1. 16-Amino-prostaglandin derivatives of general formula I

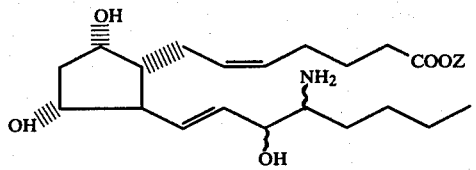

wherein C-15 and C-16 may have either S or R configuration, Z stands for a hydrogen atom or a lower alkyl group, and their acid addition salts.

2. A compound as claimed in claim 1 wherein C-16 has S configuration.

3. 9α,11α,15(S)-Trihydroxy-16(S)-amino-5-cis,13-trans-prostadienoic acid methyl ester or a pharmaceutically acceptable salt thereof.

4. 9α,11α,15(S)-Trihydroxy-16(S)-amino-5-cis,13-trans-prostadienoic acid or a pharmaceutically acceptable salt thereof.

5. 9α,11α,15(R)-Trihydroxy-16(S)-amino-5-cis-13-trans-prostadienoic acid methyl ester or a pharmaceutically acceptable salt thereof.

6. 9α,11α,15(R)-Trihydroxy-16(S)-amino-5-cis-13-trans-prostadienoic acid or a pharmaceutically acceptable salt thereof.

7. A pharmaceutical composition having abortive and oxytocic property, which comprises a pharmaceutically effective amount of a compound of the formula I as defined in claim 1 or a pharmaceutically acceptable nontoxic salt thereof.

* * * * *